United States Patent
Kimura et al.

(10) Patent No.: US 7,252,639 B2
(45) Date of Patent: Aug. 7, 2007

(54) METHOD AND APPARATUS FOR MEASURING BIOLOGICAL CONDITION

(75) Inventors: Teiyuu Kimura, Nagoya (JP); Taiji Kawachi, Kariya (JP); Kazuhiro Sakai, Kariya (JP)

(73) Assignee: DENSO Corporation, Kariya (JP)

( * ) Notice: Subject to any disclaimer, the term of this patent is extended or adjusted under 35 U.S.C. 154(b) by 480 days.

(21) Appl. No.: 10/786,156

(22) Filed: Feb. 26, 2004

(65) Prior Publication Data

US 2004/0193063 A1 Sep. 30, 2004

(30) Foreign Application Priority Data

Feb. 28, 2003 (JP) ............................. 2003-054581

(51) Int. Cl.
*A61B 5/02* (2006.01)
(52) U.S. Cl. ................. 600/500; 600/322; 600/323; 600/336
(58) Field of Classification Search ............. 600/310, 600/322, 500, 323, 336
See application file for complete search history.

(56) References Cited

U.S. PATENT DOCUMENTS

| | | | | |
|---|---|---|---|---|
| 5,046,494 A | * | 9/1991 | Searfoss et al. | 607/88 |
| 5,291,884 A | * | 3/1994 | Heinemann et al. | 600/322 |
| 5,830,137 A | * | 11/1998 | Scharf | 600/323 |
| 6,263,222 B1 | * | 7/2001 | Diab et al. | 600/310 |
| 6,709,402 B2 | * | 3/2004 | Dekker | 600/529 |
| 6,731,967 B1 | * | 5/2004 | Turcott | 600/407 |
| 6,770,036 B2 | | 8/2004 | Nakada et al. | |
| 6,997,879 B1 | * | 2/2006 | Turcott | 600/507 |
| 7,202,793 B2 | * | 4/2007 | Grace et al. | 340/576 |
| 2001/0049471 A1 | * | 12/2001 | Suzuki et al. | 600/300 |
| 2003/0229276 A1 | * | 12/2003 | Sarussi et al. | 600/322 |

FOREIGN PATENT DOCUMENTS

| | | |
|---|---|---|
| JP | 7-88092 | 4/1995 |
| JP | 7-299044 | 11/1995 |

(Continued)

OTHER PUBLICATIONS

Notification of Reasons of Rejection issued from Japanese Patent Office issued on Oct. 18, 2005 for the corresponding Japanese patent application No. 2003-054581 (a copy and English translation thereof).

*Primary Examiner*—Charles A. Marmor, II
*Assistant Examiner*—Karen E Toth
(74) *Attorney, Agent, or Firm*—Posz Law Group, PLC

(57) ABSTRACT

In an apparatus for measuring a biological condition of a living body, a light emitting unit emits individually first and second lights to a measurement portion of the living body. The first and second lights have first and second wavelengths, respectively. The first and second wavelengths are different from each other. A light receiving unit receives first and second reflection lights to generate first and second detection signals based on the first and second reflection lights, respectively. The first and second reflection lights are based on the first light reflected from the measurement portion and the second light reflected therefrom, respectively. The first and second detection signals have different characteristics from each other due to the difference between the first and second wavelengths. A measuring unit measures the biological condition based on the different characteristics of the first and second detection signals.

32 Claims, 11 Drawing Sheets

FOREIGN PATENT DOCUMENTS

| | | |
|---|---|---|
| JP | 11-128184 | 5/1999 |
| JP | 11-197126 | 7/1999 |
| JP | A-H11-276448 | 10/1999 |
| JP | A-2001-112728 | 4/2001 |
| JP | A-2002-051996 | 2/2002 |
| JP | 2003-508765 | 3/2003 |
| WO | WO 01/17420 A1 | 3/2001 |

* cited by examiner

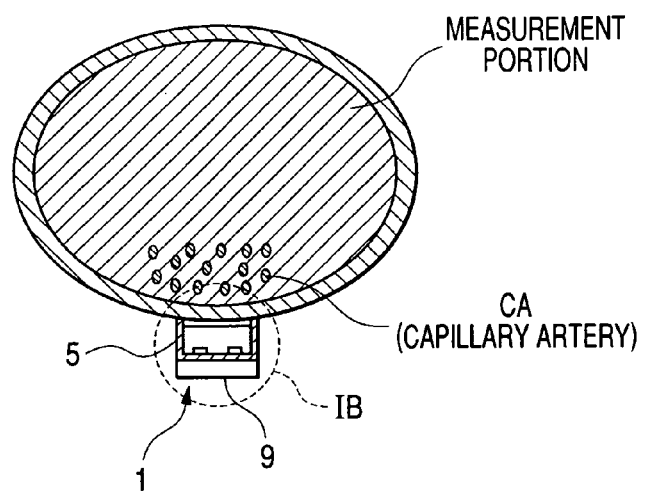
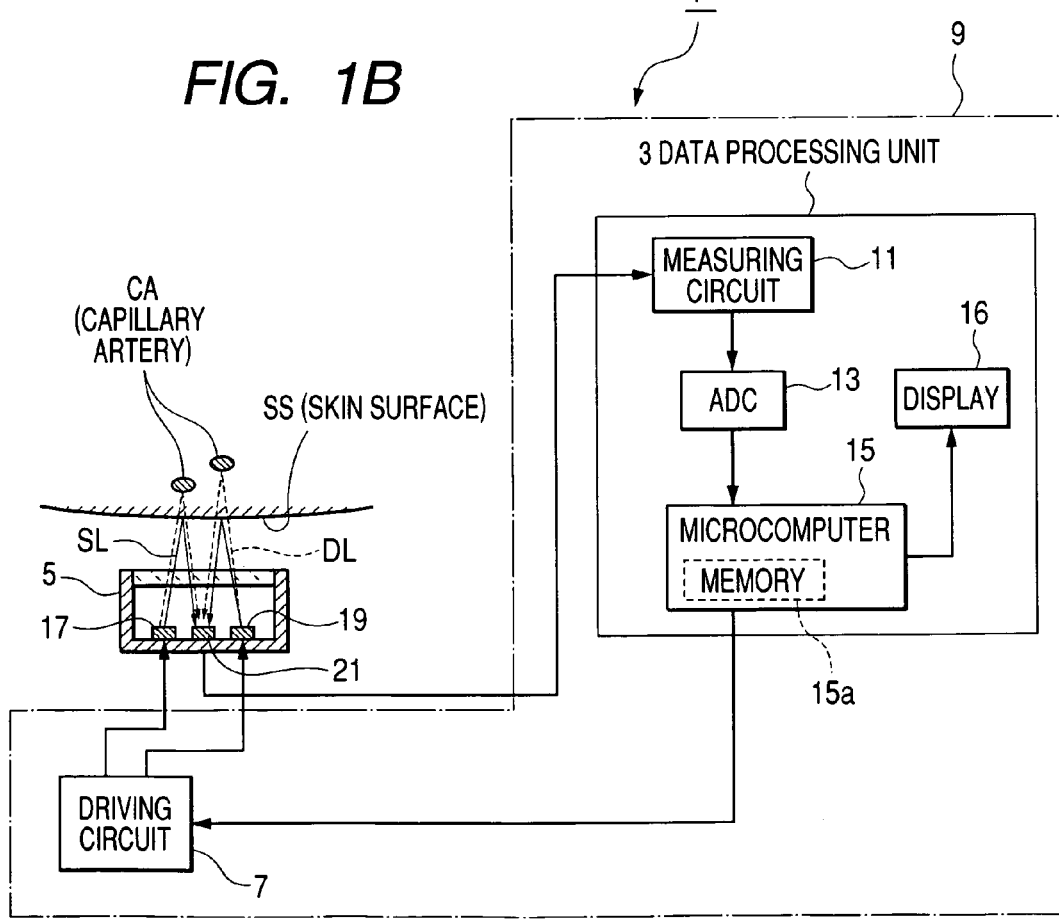

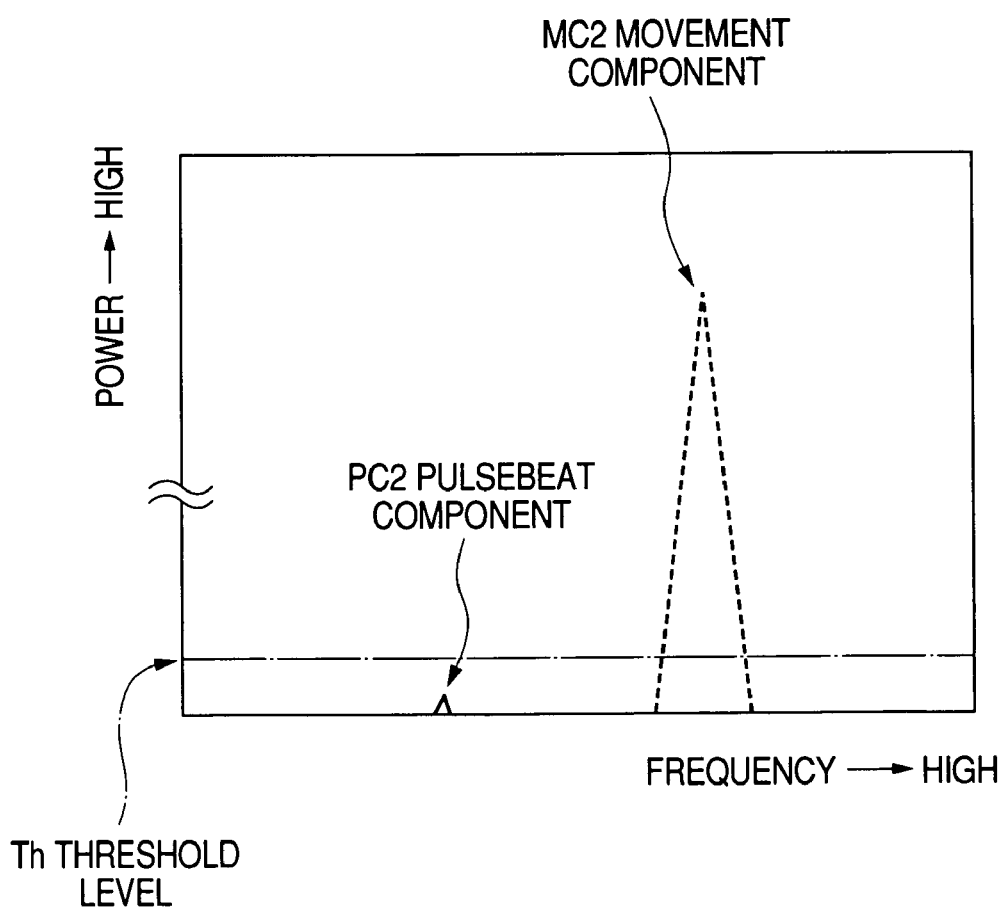

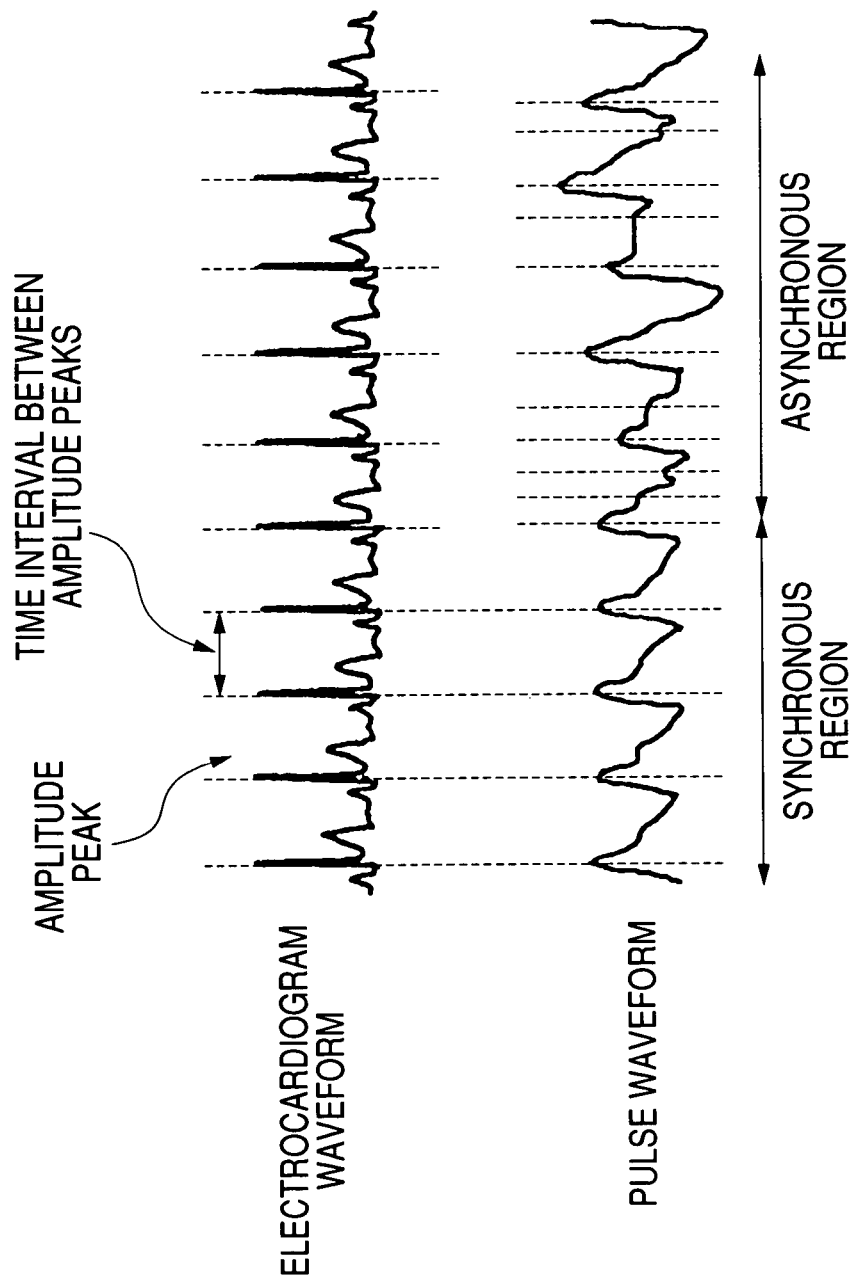

METHOD AND APPARATUS FOR MEASURING BIOLOGICAL CONDITION

BACKGROUND OF THE INVENTION

The present invention relates to a method and an apparatus for measuring a biological condition of a living body, such as the pulse rate thereof.

Recently, needs of monitoring the heartbeat rate of a living body, such as a human body, increase during exercise, such as jogging for health maintenance.

One of usual methods of measuring the heartbeat rate is to measure an action potential along with a heartbeat of a living body from the chest region to obtain an electrocardiogram, and to calculate an interval between the adjacent amplitude peaks of the electrocardiogram wave.

This method, however, when measuring the heartbeat, it is necessary to affix at least one electrode pad on a portion of the living body, and it is tedious to carry out the affixing works of the at least one electrode pad.

It is considerable to, therefore, as one of more simplified methods, measure pulse waves in the living body to detect a pulse rate of the living body based on the measured pulse waves these days.

The pulse waves are pressure fluctuations occurring in the arteries in response to the heartbeat and propagating into the peripheral arteries as wave. As one of measuring the pulse waves, an optical pulse wave sensor is well known.

The optical pulse wave sensor uses light-absorbing characteristic of hemoglobin in blood. That is, the optical pulse wave sensor irradiates light to a measurement portion of the living body to measure the volume of fluctuating blood in the peripheral arteries. The optical pulse wave sensor is easily fittable to a measurement portion of human body, such as one of the fingers, one of the arms, or one of the temples of the human body, to measure the pulse wave thereof. The optical pulse wave sensor, therefore, will become widespread as the apparatus for detecting the pulse rate.

Concretely, division of the number of 60 by a time interval between the amplitude peaks of electrocardiogram waveform (unit: second) allows the heartbeat rate (unit: pulse per minute) to be obtained. Similarly, division of the number of 60 by a time interval between the amplitude peaks of pulse waveform allows the pulse rate (unit: pulse per minute) to be obtained.

That is, the heartbeat rate and the pulse rate are represented by the following equations:

$HR$ (pulse per minute)=60/$IT1$ (second)      [Equation 1]

$PR$ (pulse per minute)=60/$IT2$ (second)      [Equation 2]

where HR represents the heartbeat rate, IT1 represents the time interval between the amplitude peaks of electrocardiogram waveform, PR represents the pulse rate, and IT2 represents the time interval between the amplitude peaks of pulse waveform.

The timing at which each amplitude peak of the electrocardiogram waveform is represented and that at which each amplitude peak of the pulse waveform is represented are usually synchronized with each other (see "synchronous region" in FIG. 16), which shows the heartbeat rate and the pulse rate are equal to each other.

The movement of the measurement portion of the living body on which the optical pulse sensor is fitted in daily life or in exercise causes the blood flowing in the peripheral arteries to be disturbed. The disturbance of the blood flow generates other amplitude peaks of the pulse waveform that are independent of the heartbeat (see "asynchronous region" in FIG. 16) so that the heartbeat rate and the pulse rate are unequal to each other. This interferes with the use of the pulse rate in substitution of the heartbeat rate.

In addition, frequencies of other amplitude peaks of the pulse waveform that are independent of the heartbeat are close to the amplitude peaks thereof that are synchronized with the amplitude peaks of the heartbeat.

This characteristic makes ineffective to use frequency-filtering operation of the pulse wave that is applied for usual noise rejection operations.

In order to solve the above problems, Japanese Patent Publication No. H07-299044 discloses the technique using an exercise noise sensor.

In this technique, the exercise noises are sensed by the exercise noise sensor as a signal related to exercise noises, and the sensed signal corresponding to the exercise noises is removed from the signal on which the exercise noises and the pulse wave signal are superimposed, allowing a pulse wave signal to be accurately detected even during exercise.

Furthermore, Japanese Patent Publication No. H07-088092 discloses the technique using different wavelength lights.

That is, the different wavelength lights are irradiated on a measurement portion of the living body to obtain signals corresponding to the different wavelength lights. The obtained signals are signal-processed to separate the pulse-wave components in the bloods from the wave components of living body's movement therein, thereby measuring the pulsebeat components.

The technique disclosed in the former Patent Publication, however, even if the exercise noise sensor can detect the exercise noises, cannot detect noises generated related to the living body itself, such as noises generated due to the light components reflected from the surface of the measurement portion, such as the skin surface thereof.

In the technique disclosed in the later Patent Publication, however, the obtained wavelength signals include the pulse wave components in the bloods and the wave components of living body's movement therein. In addition, the relationship between the pulse wave components in the bloods and the wave components of living body's movement therein changes as dependent on the fitting condition of the sensor to the living body's measurement portion, and on the individual differences among the living bodies.

Because of the change of relationship, it is difficult for the disclosed unique signal processing in the technique to accurately obtain the pulse wave components in the bloods.

SUMMARY OF THE INVENTION

The present invention is made on the background.

Accordingly, it is an object of the present invention to provide a method and an apparatus for measuring a biological condition of a living body, which are capable of reducing adverse effects on the measuring accuracy of the biological condition, thereby accurately detecting the biological condition of the living body, such as a pulsebeat thereof.

According to a first aspect of the present invention, there is provided a biological condition measuring apparatus for measuring a biological condition of a living body, the apparatus comprising: a light emitting unit configured to emit individually first and second lights to a measurement portion of the living body, the first and second lights having first and second wavelengths, respectively, the first and second wavelengths being different from each other; a light receiving unit configured to receive first and second reflection lights to generate first and second detection signals based on the first and second reflection lights, respectively, the first reflection light being based on the first light reflected from the measurement portion, the second reflection light being based on the second light reflected from the measurement portion, the first and second detection signals having different characteristics from each other due to the difference between the first and second wavelengths; and a measuring unit configured to measure the biological condition based on the different characteristics of the first and second detection signals.

According to a second aspect of the present invention, there is provided a biological condition measuring apparatus for measuring a biological condition of a living body, the apparatus comprising: a light emitting unit configured to emit individually an infrared light and a green right to a measurement portion of the living body; a light receiving unit configured to receive first and second reflection lights to generate first and second detection signals based on the first and second reflection lights, respectively, the first reflection light being based on the infrared light reflected from the measurement portion, the second reflection light being based on the green light reflected from the measurement portion, the first and second detection signals having different characteristics from each other due to the difference between wavelengths of the infrared light and the green light; and a measuring unit configured to measure the biological condition based on the different characteristics of the first and second detection signals.

According to a third aspect of the present invention, there is provided a sensor for sensing a biological condition of a living body, the sensor comprising: a housing having a first wall, a second opened wall opposite to the first wall, and a window wall fitted to the second opened wall; a light emitting unit contained in the housing and configured to emit individually first and second lights through the window wall to a measurement portion of the living body, the first and second lights having first and second wavelengths, respectively, the first and second wavelengths being different from each other; and a light receiving unit contained in the housing and configured to receive first and second reflection lights to generate first and second detection signals based on the first and second reflection lights, respectively, the first reflection light being based on the first light reflected through the window wall from the measurement portion, the second reflection light being based on the second light reflected through the window wall from the measurement portion, the first and second detection signals having different characteristics from each other due to the difference between the first and second wavelengths, wherein the window wall is provided at its an outer end surface with a stepped portion, the stepped portion includes a first surface, and a second surface through which the first light and the first reflection light are transmitted, the stepped surface being stepped inwardly with respect to the first surface.

According to a fifth aspect of the present invention, there is provided a sensor for sensing a biological condition of a living body, the sensor comprising: a housing having a first wall, a second opened wall opposite to the first wall, and a window wall fitted to the second opened wall; a light emitting unit contained in the housing and configured to emit individually first and second lights through the window wall to a measurement portion of the living body, the first light having a first wavelength, the second light having a second wavelength, the first and second wavelengths being different from each other; and a light receiving unit configured to receive first and second reflection lights to generate first and second detection signals based on the first and second reflection lights, respectively, the first reflection light being based on the first light reflected through the window wall from the measurement portion, the second reflection light being based on the second light reflected through the window wall from the measurement portion, the first and second detection signals having different characteristics from each other due to the difference between the first and second wavelengths, wherein the window wall has an outer end surface, the outer end surface includes a first surface and a second surface through which the first light and the first reflection light are transmitted, and the second surface is formed with concave and convex portions.

According to a sixth aspect of the present invention, there is provided a method of measuring a biological condition of a living body, the method comprising: individually emitting first and second lights to a measurement portion of the living body, the first and second lights having first and second wavelengths, respectively, the first and second wavelengths being different from each other; receiving first and second reflection lights to generate first and second detection signals based on the first and second reflection lights, respectively, the first reflection light being based on the first light reflected from the measurement portion, the second reflection light being based on the second light reflected from the measurement portion, the first and second detection signals having different characteristics from each other due to the difference between the first and second wavelengths; and measuring the biological condition based on the different characteristics of the first and second detection signals.

According to a seventh aspect of the present invention, there is provided a program product readable by a computer communicable with a light emitting unit and a light receiving unit, the light emitting unit being configured to emit individually first and second lights to a measurement portion of the living body, the first and second lights having first and second wavelengths, respectively, the first and second wavelengths being different from each other, the light receiving unit being configured to receive first and second reflection lights to generate first and second detection signals based on the first and second reflection lights, respectively, the first reflection light being based on the first light reflected from the measurement portion, the second reflection light being based on the second light reflected from the measurement portion, the first and second detection signals having different characteristics from each other due to the difference between the first and second wavelengths, the program product configured to cause the computer to: control the light emitting unit so that the light emitting unit controls that at least one of an intensity and an amount of the first light is lower than at least one of an intensity and an amount of the second light, and the different characteristics of the first and second detection signals are based on the difference of the first and second wavelengths, and the difference between the at least one of the intensity and the amount of the first light and the at least one of the intensity and the amount of the second light; compare the characteristic of the first detection signal with that of the second detection signal; and extract a signal from the first and second detection signals according to a result of the comparing, the extracted signal representing the biological condition.

BRIEF DESCRIPTION OF THE DRAWINGS

Other objects and aspects of the invention will become apparent from the following description of an embodiment with reference to the accompanying drawings in which:

FIG. 1A is a view illustrating such a state that a biological condition measuring apparatus according to a first embodiment of the invention is fitted to a measurement portion of a human body;

FIG. 1B is an enlarged view illustrating a portion IB illustrated in FIG. 1A and a block structure of the measuring apparatus illustrated in FIG. 1A;

FIG. 11 is a graph illustrating changes in time of the pulsebeat component and the movement component based on the infrared light and a threshold level according to the third embodiment;

FIG. 16 is a view illustrating an electrocardiogram waveform and a pulse waveform obtained in a conventional optical pulse sensor.

DETAILED DESCRIPTION OF EMBODIMENTS OF THE INVENTION

Figure 2:
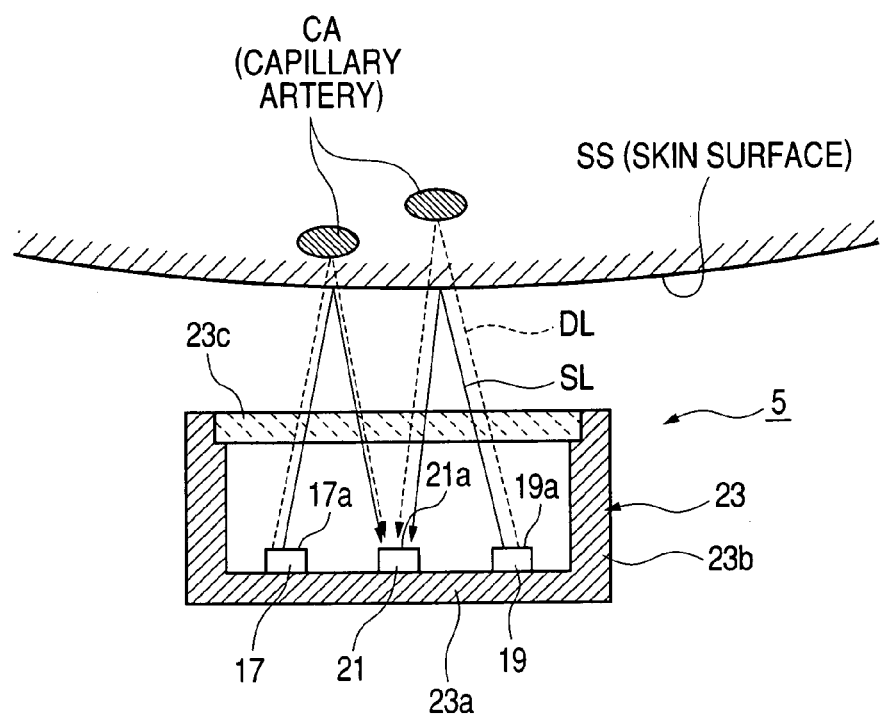
FIG. 2 is an enlarged view illustrating the pulse wave sensor illustrated in FIGS. 1A and 1B.

Embodiments of the invention will be described hereinafter with reference to the accompanying drawings.

First Embodiment

FIG. 1A is a view illustrating such a state that a biological condition measuring apparatus for executing a pulse wave measuring method as a biological condition measuring method according to a first embodiment of the invention is fitted to a measurement portion MP of a living body, such as a human body. FIG. 1B is a block diagram of the measuring apparatus illustrated in FIG. 1A, which is capable of detecting, as a biological condition, a pulse wave of the human body.

The measuring apparatus 1, as shown in FIG. 1, is composed of a data processing unit 3, a pulse wave sensor 5 communicable with the data processing unit 3, and a driving circuit 7 communicable with the data processing unit 3.

The data processing unit 3 includes a measuring circuit 11 having a cut-off filter for allowing some components of a signal inputted from the pulse wave sensor 5 that are not less than a predetermined cut-off frequency and cutting off other components that are less than the predetermined cut-off frequency. The measuring circuit 11 is configured to amplify the some components of the signal, and an analog-to digital (A/D) converter 6 electrically connected thereto and configured to convert the amplified components of the signal into digital data.

The data processing unit 3 also includes a microcomputer 15 electrically connected to the A/D converter 13.

The data processing unit 3 further includes a display, such as a liquid crystal display, 16 electrically connected to the microcomputer 15 and configured to display data transmitted from the microcomputer 15.

The pulse wave sensor 5, which is optical reflection sensor, is provided with a housing 23 having a substantially rectangular solid shape with one opened end wall, an infrared LED (light emitting device) 17 and a green LED 19, which are installed in the housing 23 and served as light emitting elements. The pulse wave sensor 5 is also provided with a photo diode (PD) 21 as a light sensitive element, which is installed in the housing 23.

The driving circuit 7 is operative to supply driving voltages to the infrared LED 17 and the green LED 19 at different timings, respectively, thereby causing the infrared LED 17 and the green LED 19 to emit light at different timings, respectively.

The data processing unit 3 and the driving circuit 7 are contained in a housing of an apparatus body 9 of the measuring apparatus 1.

Next, the structure of the pulse wave sensor 5 will be explained in detain hereinafter.

The pulse wave sensor 5 is fittable to the measurement portion MP of the human body, such as the right or left arm, the brow, and the right or left temple of the human body. The back of the wrist or the upper arm is preferable to fit the pulse wave sensor 5 thereto.

In this first embodiment, the pulse wave sensor 5 is fitted to a portion of light or left arm of the human body, which is the measurement portion MP thereof.

The infrared LED 17 is configured to irradiate an infrared light with a wavelength of approximately 940 nm from its emitting portion 17a. The green LED 19 is configured to irradiate a green light with a wavelength that is different from the wavelength of the infrared light from its emitting portion 19a.

That is, the wavelength of the green light is lower than that of the infrared light, such as approximately 520 nm.

The PD 21 is configured to receive, through its light sensitive portion 21a, reflection lights that are based on the infrared light and the green light reflected from the inside of the measurement portion MP of the human body, respectively.

The housing 23 is composed of a bottom wall 23a opposite to the opened wall and a side wall portion 23b extending from the bottom wall 23a to the opened wall portion, and a transparent window wall 23c made of, for example, transparent and translucent material, such as transparent resin, attached fittedly to the opened end wall.

When measuring the pulse wave of the human body, the pulse wave sensor 5 is fitted to the measurement portion MP of the human body, so that the outer surface of the transparent window wall 23c is located to be opposite to the measurement portion MP of the human body, or that the outer end surface of the transparent window wall 23c is directly contacted to the measurement portion MP thereof.

When the pulse wave sensor 5 is fitted to the measurement portion MP, the inner surface of the bottom wall 23a is opposite through the transparent window wall 23c to the skin surface SS of the measurement portion MP.

The infrared LED 17, the green LED 19, and the PD 21, as shown in FIGS. 1A, 1B, and 2, are mounted on the inner surface of the bottom wall 23a of the housing 13. When the pulse wave sensor 5 is fitted to the measurement portion MP, their light-emitting portions 17a and 19a, and the light sensitive portion 21a of the PD 21 are opposite through the transparent window wall 23c to the skin surface SS of the measurement portion MP.

The infrared LED 17, the green LED 19, and the PD 21 are arranged in a row so that the infrared LED 17 and the green LED 19 are located at both sides of the PD 21.

That is, the infrared LED 17 and the green LED 19 individually irradiate the infrared light and the green light through the transparent window wall, respectively.

When the light, such as the infrared light or the green light is irradiated, some of the irradiated light enters into the inside of the measurement portion MP, and the reminder thereof is reflected from the skin surface SS of the measurement portion MP.

Some of the entered light strikes the small arteries and arterioles (capillary arteries) flowing inside of the measurement portion MP, and some of the struck light is absorbed in hemoglobin in the blood flowing in the capillary arteries CA, and the remainder of the entered light is reflected from the capillary arteries CA to be scattered. Some of the scattered light enters into the PD 21.

The volume of hemoglobin in the capillary arteries CA fluctuates in response to the pulsation of blood flowing therein so that the amount of light absorbed in the hemoglobin also fluctuates.

In addition, the volume of hemoglobin in the capillary arteries CA also fluctuates due to the change of each capillary artery's diameter.

These fluctuations of hemoglobin's volume, that is, moves in pulse waves cause the amount of light detected by the PD 21 to move in pulse waves, so that the change of the amount of detected light is transmitted to the data processing unit 3 as pulse wave information, such as voltage signal.

Thus, the voltage signal corresponding to the reflected light of the infrared light from the infrared LED 17 and that corresponding to the reflected light of the green light from the green LED 19 are received by the data processing unit 3, respectively. The data processing unit 3 can operate based on the detection signals in accordance with the pulse wave measuring method described hereinafter to obtain the biological condition of the human body, such as the pulse rate.

Incidentally, in FIGS. 1B and 2, some of reflected light from the capillary arteries CA is represented as dashed lines DL, and some of reflected light from the skin surface SS is represented as solid lines SL.

Next, the principal of measuring the pulse wave according to the first embodiment will be explained hereinafter.

Figure 3:
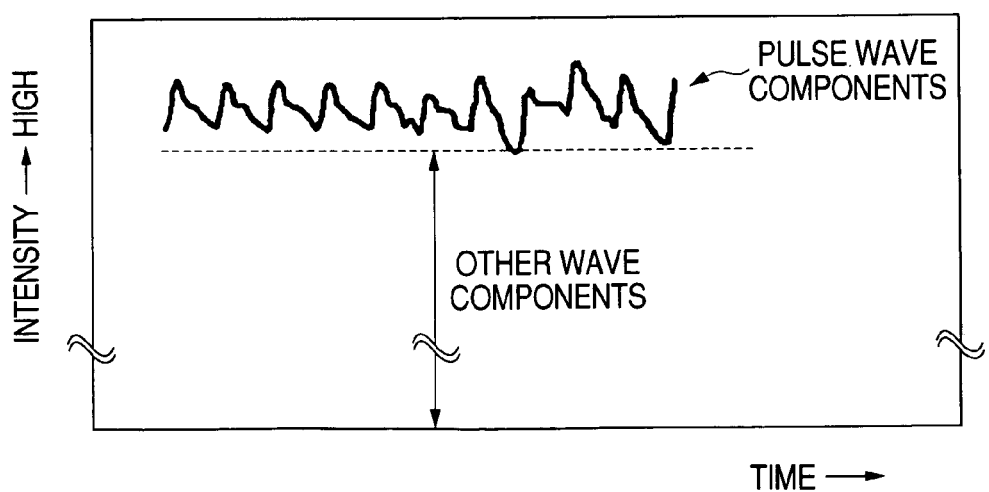
FIG. 3 is a graph illustrating a waveform representing a relationship between intensity of a detection signal inputted by a data processing unit and time according to the first embodiment.

FIG. 3 illustrates the waveform representing the relationship between the intensity of the detection signal inputted by the data processing unit 3 and time. The intensity of the detection signal, as shown in FIG. 3, contains the intensity of the signal representing the pulse wave components reflected from the capillary arteries CA and that of the signal representing other wave components reflected from the skin surface SS or other portions in the measurement portion MP except for the capillary arteries CA.

Figure 4:
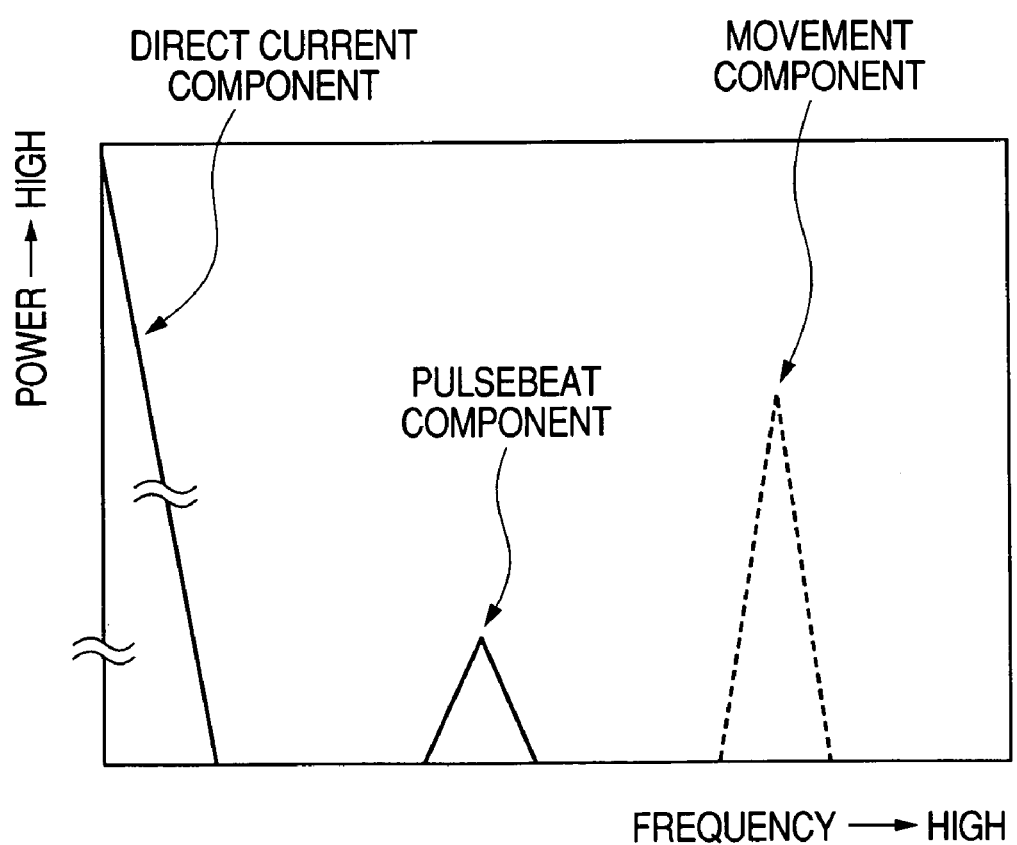
FIG. 4 is a graph illustrating a result of frequency analysis of the detection signal according to the first embodiment.

FIG. 4 illustrates a result of frequency analysis of the detection signal. That is, in FIG. 4, the power spectrum of the detection signal, that is, the power levels of the frequency components thereof are represented.

As shown in FIG. 4, the detection signal in frequency domain contains three peak frequency components: the pulsebeat component synchronized with the heartbeat, the component of the human body's movement synchronized with the human body's movement, and the direct current component corresponding to other wave components except for the component of the human body's movement.

The frequency band of the direct current component is widely different from those of the pulsebeat component and the component of the human body's movement so that setting the cut-off frequency that is close to and not less than the frequency band of the direct current components allows the direct current component to be effectively cut-off.

In addition, the pulsebeat component synchronized with the heartbeat has the characteristic that it rides on the pulse wave component shown in FIG. 3, and the component of the human body's movement, which is referred to as "movement component" hereinafter, rides on both of the pulse wave and the other waves shown in FIG. 3.

Figure 5A:
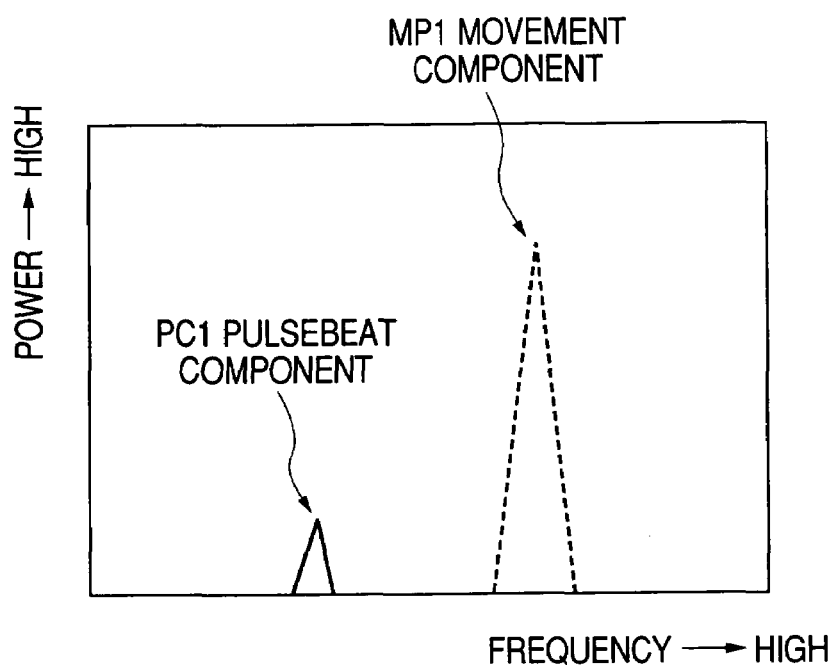
FIG. 5A is a graph illustrating a result of the frequency analysis of the detection signal based on a green light according to the first embodiment.

On the other hand, as shown in FIG. 5A, when the green light is irradiated from the green LED 19 so that the pulsebeat component PC1 and the movement component MC1 are measured based on the green light, the ratio of the power of the pulsebeat component PC1 illustrated in solid line to that of the movement component illustrated in dashed line is approximately 1:5.

Figure 5B:
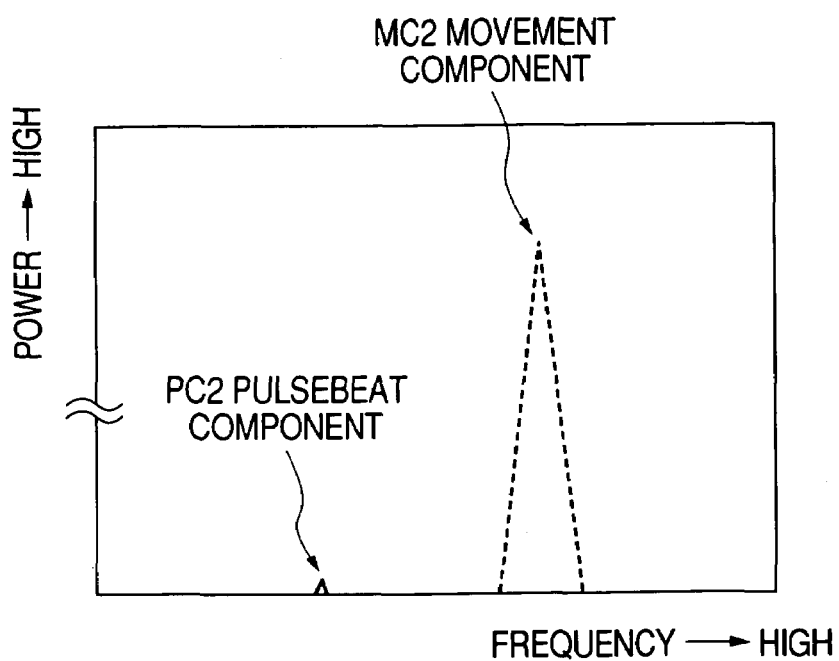
FIG. 5B is a graph illustrating a result of the frequency analysis of the detection signal based on an infrared light according to the first embodiment.

In contrast, as shown in FIG. 5B, when the infrared light is irradiated from the infrared LED 17 so that the pulsebeat component PC2 and the movement component MC2 are measured based on the infrared light, the ratio of the power of the pulsebeat component PC2 illustrated in solid line to that of the movement component MC2 illustrated in dashed line is approximately 1:50.

That is, when using the long wavelength light, such as the infrared light, as compared with the green light, the pulsebeat component PC2 is significantly reduced as compared with the movement component MC2.

In this first embodiment, based on the relationships between the ratio obtained by using the green light and that obtained by using the infrared light, the intensity of the infrared light irradiated from the infrared LED 17 is sufficiently reduced as compared with that of the green right irradiated from the green LED 19. In particular, the driving circuit 7 controls the driving voltages with respect to the infrared LED 17 and the green LED 19 so that the intensity of the infrared light irradiated from the infrared LED 17 is reduced to approximately one-fifth of the intensity of the green light irradiated from the infrared LED 17.

Concretely, the driving circuit 7 controls that the driving voltage applied on the infrared LED 17 is lower than the driving voltage applied on the green LED 19. In other means for reducing the intensity of the infrared light, an infrared LED having the rated intensity lower than that of the green LED may be used.

This control of the infrared light intensity allows the pulse rate component based on the infrared light to be buried in the noise components contained in the detection signal corresponding to the infrared light and measured by the measuring circuit 11. That is, when the infrared light is irradiated from the infrared LED 17, because the noise components substantially fail to be measured by the measuring circuit 11, the movement component is substantially only measured by the measuring circuit 11. In particular, setting the infrared light intensity of the infrared LED 17 to one-fifth of the green light intensity of the green LED 19 is suitable because of making it easy to extract the movement component.

As described above, comparing the frequency components containing the pulsebeat component and the movement component based on the green light of the green LED 19 as those containing only the movement component based on the infrared light of the infrared LED 17 permits only the pulsebeat component to be extracted.

Next, procedures of measuring the pulsebeat component according to the first embodiment will be explained hereinafter in accordance with FIG. 6.

Figure 6:
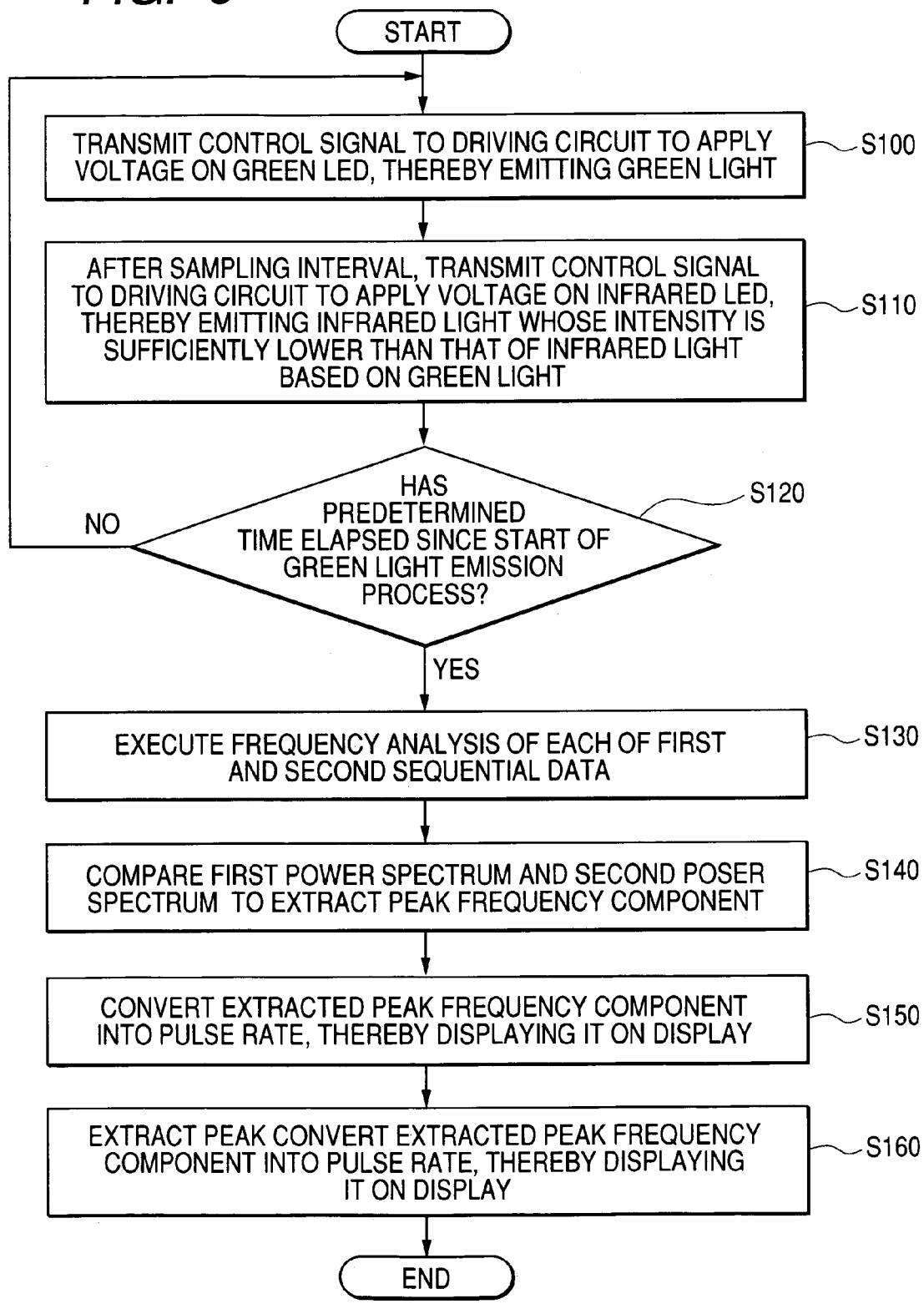
FIG. 6 is a flowchart illustrating pulse wave measuring processes of a data processing unit (microprocessor) illustrated in FIG. 1B according to the first embodiment.

The microcomputer operates in accordance with the program algorism) stored on the memory 15a to execute the pulsebeat measuring processes illustrated in FIG. 6.

That is, in Step S100 in FIG. 6, the microcomputer 15 transmits the control signal to the driving circuit 7 so that the driving circuit 7 applies the driving voltage on the green LED 19 to cause the green LED 19 to emit the green light once. As described above, some of the emitted green light enters into the inside of the measurement portion MP, and the reflection light reflected from the measurement portion MP and including the direct current component, the pulsebeat component and the movement component is detected by the PD 21. The detection signal corresponding to the reflection light based on the green light is transmitted to the measuring circuit 11, and the direct current component of the detection signal is cut off.

The detection signal whose direct current component is cut off is amplified by the measuring circuit 11 and converted into the digital data by the A/D converter 13, thereby being inputted to the microcomputer 15.

The digital data corresponding to the detection signal based on the green light is stored by the microcomputer 15 on its memory 15a.

In next Step S110, after a predetermined sampling interval, such as 50 milliseconds [msec], has elapsed from the emission of the green LED 17, the microcomputer 15 transmits the control signal, which allows the intensity of the infrared light emitted from the infrared LED 17 to be set to one-fifth intensity of the green light, to the driving circuit 7. In response to the control signal, the driving circuit 7 applies the driving voltage on the infrared LED 17 to cause the infrared LED 17 to emit once the infrared light whose intensity is one-fifth of the intensity of the emitted green light.

Similarly, to the green light, some of the emitted infrared light enters into the inside of the measurement portion MP.

As described above, because the intensity of the infrared light is one-fifth of the intensity of the green light, the reflection light reflected from the measurement portion MP includes the direct current component and the movement component except for the pulsebeat component. The reflection light is detected by the PD 21. The detection signal corresponding to the reflection light based on the infrared light is transmitted to the measuring circuit 11, and the direct current component of the detection signal is cut off.

The detection signal whose direct current component is cut off is amplified by the measuring circuit 11 and converted into the digital data by the A/D converter 13, thereby being inputted to the microcomputer 15.

The digital data corresponding to the detection signal based on the infrared light is stored by the microcomputer 15 on its memory 15a.

In Step S120, the microcomputer 15 determines whether a predetermined time, such as approximately 25 seconds, has elapsed since the start of green light emission process. If the predetermined time has not elapsed (the determination in Step S120 is NO), the microcomputer 15 returns to the process in Step S100 and repeats the light emitting processes in Step S100 and S110.

That is, the microcomputer 15 causes, through the driving circuit 7, the green LED 17 and the infrared LED 19 to alternatively emit the green light and the infrared light at the predetermined intervals of 50 [msec], in other words, at predetermined periods of 20 hertz [Hz].

As a result, the digital data corresponding to the detection signal based on the green light is sequentially stored on the memory 15a as first sequential data in time domain, and the digital data corresponding to the detection signal based on the infrared light is sequentially stored on the memory 15a as second sequential data in time domain.

These emission controls can prevent the detection signals based on both of the green light and the infrared light from being simultaneously detected by the PD 21.

If the predetermined time has elapsed (the determination in Step S120 is YES), that is, the first and second sequential data based on the green light and the infrared light during the approximately 25 seconds is stored on the memory 15a, the microcomputer 15 shift to the process in Step S130.

Note that the first and second sequential data stored on the memory 15a during the approximately 25 seconds is sufficient to measure the pulsebeat component and/or the frequency band of the movement component.

In Step S130, the microcomputer 15 executes the frequency analysis of each of the first sequential data and the second sequential data that are obtained based on the green light and the infrared light, respectively.

That is, the microcomputer 15 executes one of well-known frequency analyses, such as the Fast Fourier Transformation (FFT), on the first sequential data to obtain a first power spectrum of the frequency components of the first sequential data in frequency domain (see FIG. 5A). Similarly, the microcomputer 15 executes the Fast Fourier Transformation (FFT) on the second sequential data to obtain a second power spectrum of the frequency components of the second sequential data in frequency domain (see FIG. 5B).

That is, as shown in FIG. 5A, in the first power spectrum, the peak frequency component (the pulse beat component) PC1 and the peak frequency component (the movement component) MC1 based on the green light are obtained.

In contrast, as shown in FIG. 5B, in the second power spectrum, because the pulsebeat component based on the infrared light is sufficiently reduced as compared with the pulsebeat component based on the green light, only one peak frequency component (the movement component) MC2 based on the infrared light is obtained.

Consequently, in Step S140, the microcomputer 15 compares the obtained first power spectrum based on the first sequential data with the obtained second power spectrum based on the second sequential data to extract the peak frequency component that does not exist in the second power spectrum, but exist in the first power spectrum.

Figure 7:
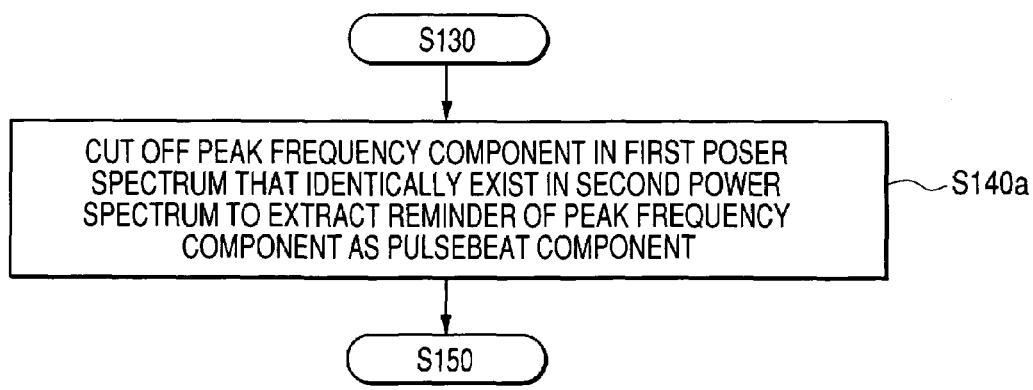
FIG. 7 is a flowchart illustrating a concrete process of Step S140 in FIG. 6.

In a concrete process in Step S140, the microcomputer 15 cuts off the peak frequency component MC1 in the first power spectrum that identically exist in the second power spectrum as the peak frequency component MC2, thereby extracting the reminder of peak frequency component PC1 as the pulsebeat component in Step S140a of FIG. 7.

In Step S150, the microcomputer 15 converts the extracted peak frequency component into a pulse rate, thereby displaying the pulse rate on the display 16.

In a concrete process in Step S150, the microcomputer 15 multiplies the extracted frequency component by 60 seconds to calculate the pulse rate. For example, assuming that the extracted peak of pulse frequency component is 1 [Hz], multiplying 1 [Hz] by 60 [seconds] can calculate the pulse rate of 60 [unit: pulse per minute]. The interval between adjacent pulsebeats can be obtained as the reciprocal value of the extracted peak frequency component.

In Step S160, the microcomputer 15 extracts the peak frequency component MC2 in the second power spectrum to convert it into a human body movement rate, thereby displaying the human body movement rate on the display 16. The microcomputer 15 terminates the processes of obtaining the pulsebeat component.

Figure 8A:
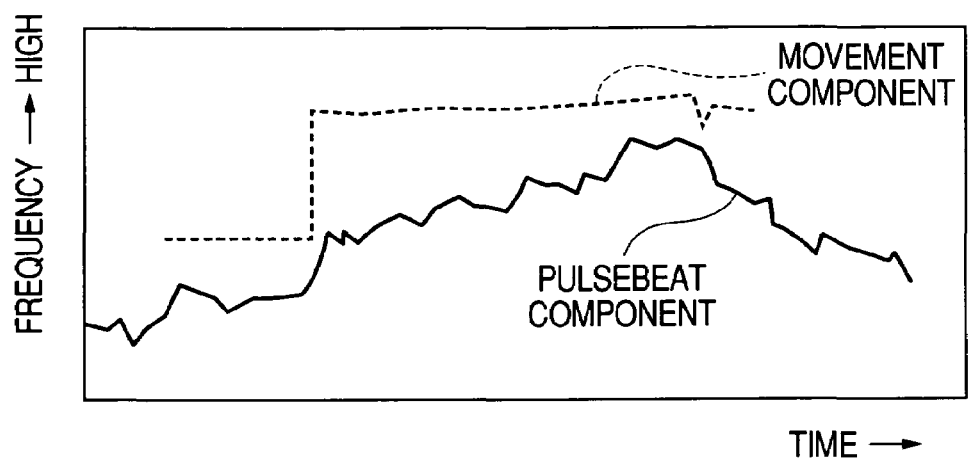
FIG. 8A is a graph illustrating changes in time of pulsebeat component and a movement component based on the green light.

In a concrete process in Step S160, the microcomputer 15 multiplies the extracted frequency component by 60 seconds to calculate the rate of human body's movement, While the pulse wave sensor 5 is actually fitted to the measurement portion MP of the human body with the human body moving, changes in time of the obtained frequency components by the above frequency analysis based on the green light are illustrated in FIG. 8A. Similarly, while the pulse wave sensor 5 is actually fitted to the measurement portion MP of the human body with the human body moving, change in time of the obtained frequency component by the above frequency analysis based on the infrared light is illustrated in FIG. 8B.

As shown in FIG. 8A, the peak frequency component (pulsebeat component) PC1 and the peak frequency component (movement component) MC1 individually continuously change in time.

Figure 8B:
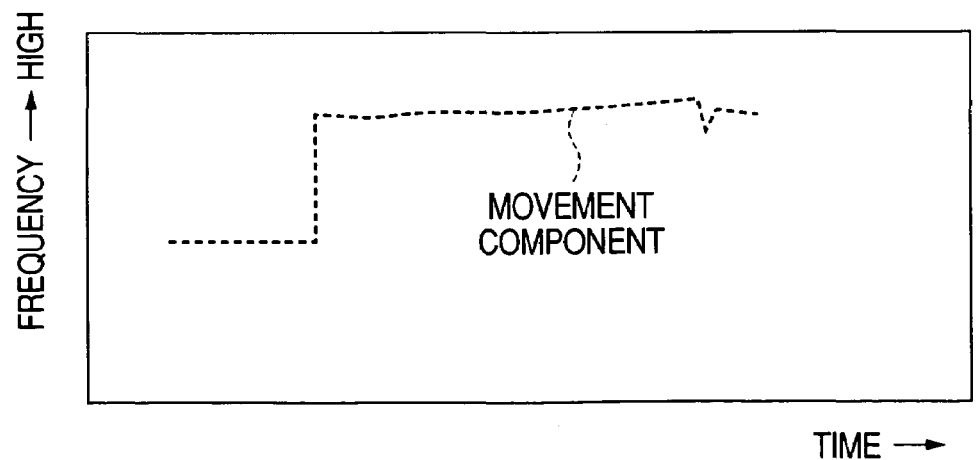
FIG. 8B is a graph illustrating changes in time of the pulsebeat component and the movement component based on the infrared light.

In contrast, as shown in FIG. 8B, only the peak frequency component (movement component) MC2 continuously changes in time.

Consequently, as clearly understood in FIGS. 8A and 8B, comparing the graph representing the changes of the peak frequency components PC1 and MC1 based on the green light with the graph representing the change of the peak frequency component MC2 based on the infrared light allows only the pulsebeat component to be extracted, thereby calculating the pulse rate. In addition, the rate of the human body's movement is also calculated based on the change of the peak frequency component MC2.

According to the first embodiment, as described above, the green light from the green LED 19 and the infrared light from the infrared LED 17 are individually irradiated at the different timings to the measurement portion MP of the human body while decreasing the intensity of the infrared light to approximately one-fifth of the green light's intensity. In addition, the lights reflected from the measurement portion MP based on the green light and the irradiated light are detected by the PD 21.

The detection signals by the PD 21 based on the reflected lights are transmitted through the measuring circuit 11 and the A/D converter 13 to the microcomputer 15 as the first and second sequential data. The first and second sequential data based on the green light and the infrared light are frequency-analyzed so that the pulsebeat components and the movement components are obtained.

Then, in the result of the frequency-analysis on the detection signal based on the infrared light, the movement component is substantially only represented, but, in the result of the frequency-analysis on the detection signal based on the green light, both the pulsebeat component and the movement component are represented.

Comparing, therefore, the result of the frequency-analysis based on the infrared light with the result of the frequency-analysis based on the green light enables only the pulsebeat component to be extracted.

In addition, the pulse rate and the interval between adjacent pulsebeats can be obtained from the extracted pulsebeat component, and the movement component and the rate of the human body's movement.

Moreover, in the first embodiment, though the pulse wave sensor 5 has such a very simple structure that includes at least two LEDs 17 and 19 and at least one PD 21, this simple structure allows the pulsebeat component, the pulse rate, and the rate of the human body's movement to be measured, respectively.

In particular, the PD 21 is operative to detect both of the reflection light based on the infrared light and the reflection light based on the green light, making it possible to more simplify the structure of the pulse wave sensor 1.

Incidentally, in the first embodiment, as an example of the measuring process of the pulsebeat component, the infrared light's intensity is controlled to be reduced. However, as another example of the measuring process, an infrared LED capable of emitting low amount of light as compared with the green LED may be used for reducing the amount of light from the infrared LED. Preferably, the infrared LED may be capable of emitting the infrared light whose amount is one-fifth of the amount of the green light emitted from the green LED.

Second Embodiment

A second embodiment of the present invention will be described hereinafter.

In the second embodiment, elements of a biological condition measuring apparatus according to the second embodiment that are the same as those of the biological condition measuring apparatus 1 according to the first embodiment are omitted or simplified.

In this second embodiment, the infrared LED 17 and the green LED 19 emit the infrared light and the green light that have substantially same intensity, respectively.

The reflected lights based on the infrared light and the green light are detected by the PD 21, and the detection signals by the PD 21 are inputted to the measuring circuit 11, so that the measuring circuit 11 cuts off the direct current components of the detection signals, respectively, which is similar to the measuring process of the first embodiment.

Figure 9:
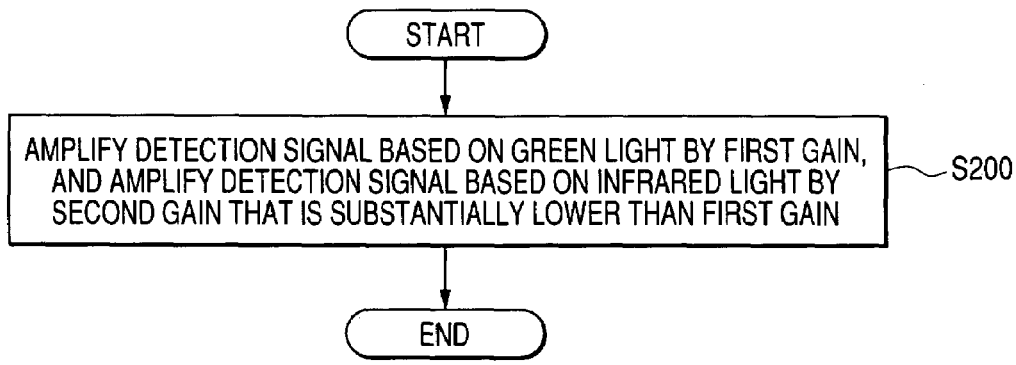
FIG. 9 is a flowchart illustrating a part of the pulse wave measuring processes of the data processing unit (measuring circuit) illustrated in FIG. 1B according to a second embodiment of the present invention.

Then, in this second embodiment, the measuring circuit 11, in order to change the sensitivity of the detection signal based on the infrared light with respect to that of the detection signal based on the green light, amplifies the detection signal based on the green light by a first gain, and amplifies the detection signal based on the infrared light by a second gain which is lower than the first gain in Step S200 of FIG. 9.

In particular, the second gain is sufficiently lower than the first gain. Preferably, the second gain is set to be one-fifth of the first gain, that is, approximately 20% of the first gain.

This sensitivity changing process (gain control process), as the same as the first embodiment, allows, when the infrared light is irradiated from the infrared LED 17, the pulsebeat component in the detection signal based on the infrared light to be buried in the noise components contained in the detection signal corresponding to the infrared light and measured by the measuring circuit 11.

As a result, when the infrared light is irradiated from the infrared LED 17, it is possible to measure only the movement component, and therefore, based on the extracted movement component, it is possible to measure the pulsebeat component, the pulse rate, and the rate of the human body's movement, which is similar to the first embodiment.

Third Embodiment

A third embodiment of the present invention will be described hereinafter.

In the third embodiment, elements of a biological condition measuring apparatus according to the third embodiment that are the same as those of the biological condition measuring apparatus 1 according to the first embodiment are omitted or simplified.

The infrared LED 17 and the green LED 19 emit the infrared light and the green light that have substantially same intensity, respectively.

The reflected lights based on the infrared light and the green light are detected by the PD 21. The detection signals by the PD 21 are inputted to the measuring circuit 11. The direct current components of the detection signals are cut off, respectively, and they are amplified by the measuring circuit 11 by the same gain, respectively.

The amplified detection signals are transmitted to the microcomputer 15, and are frequency-analyzed thereby so that the pulsebeat components and the movement components are obtained (see Steps S100-S130).

Figure 10:
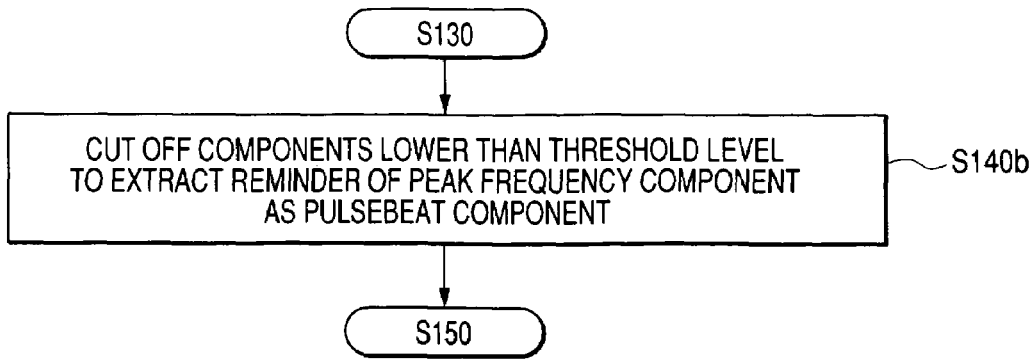
FIG. 10 is a flowchart illustrating another concrete process of Step S140 in FIG. 6 according to a third embodiment of the present invention.

Then, in this third embodiment, as the comparing process in Step S140, the microcomputer 15, because the power level of the peak frequency component PC2 corresponding to the pulsebeat component is remarkably low, cuts off the components lower than a threshold level Th to extract only the movement component MC2 in Step S140*b* of FIG. 10 (see FIG. 11). The threshold power level is set to be less than the power level of the peak frequency component MC2 corresponding to the movement component, and to be more than the power level of the peak frequency component corresponding to the pulsebeat component.

Similarly, in the third embodiment, based on the extracted movement component MC2, it is possible to measure the pulsebeat component, the pulse rate, and the rate of the human body's movement, which is similar to the first embodiment.

Fourth Embodiment

A fourth embodiment of the present invention will be described hereinafter.

In the fourth embodiment, elements of a pulse wave sensor according to the fourth embodiment that are the same as those of the pulse wave sensor 5 according to the first embodiment are omitted or simplified.

Figure 12:
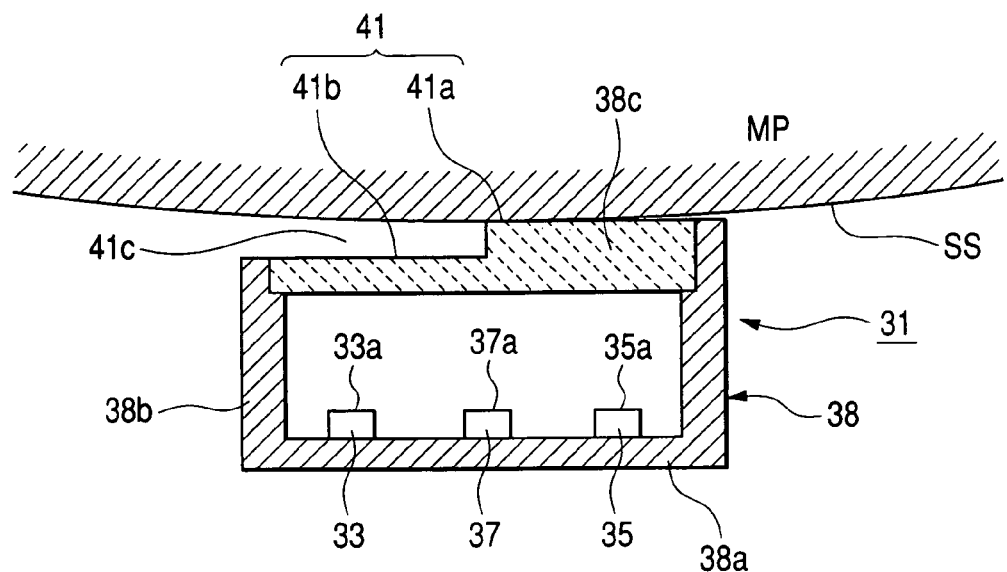
FIG. 12 is an enlarged view illustrating a pulse wave sensor according to a fourth embodiment of the present invention.
Figure 13:
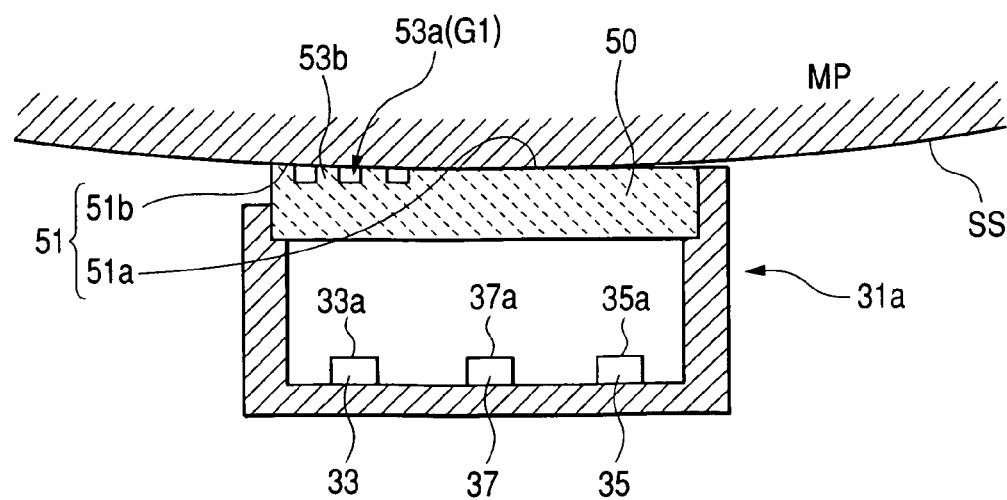
FIG. 13 is an enlarged view illustrating a modification of the pulse wave sensor illustrated in FIG. 12.

As shown in FIG. 12, the pulse wave sensor 31 according to the fourth embodiment is composed of an infrared LED 33 with its emitting portion 33*a* corresponding to the infrared LED 17, a green LED 35 with its emitting portion 35*a* corresponding to the green LED 19, and a PD 37 with its light sensitive portion 37*a* corresponding to the PD 21.

Similarly, the pulse wave sensor 31 is provided with a housing 38 corresponding to the housing 23. The housing 38 is composed of a bottom wall 38*a* corresponding to the bottom wall 23*a*, a side wall portion 38*b* corresponding to the side wall portion 23*b*, and a transparent window wall 38*c* corresponding to the transparent window wall 23*c*.

In this fourth embodiment, the transparent window wall 38*c* is formed at its outer end side with a stepped portion 41. The stepped portion 41 includes a first surface 41*a* opposite to at least the green LED 35 so that the green light and the reflection light based on the green light are transmitted through the first surface 41*a*.

The stepped portion 41 also includes a second stepped surface 41*b* opposite to at least the infrared LED 33 and stepped (recessed) inwardly. That is, the infrared light and the reflection light based on the infrared light are transmitted through the second stepped surface 41*b*.

The stepped portion 41 is formed by concavely notching a part of its outer end surface facing the infrared LED 33.

That is, when the pulse wave sensor 31 is fitted to the measurement portion MP of the human body so that the first surface 41*a* of the transparent window wall 38*c* contacts to the skin surface SS of the measurement portion MP, the second stepped surface 41*b* provides a concave portion (gap) 41*c* with respect to the skin surface SS, allowing the second surface 41*b* of the transparent window wall 38*c* not to directly contact to the human body.

This structure enables a part of the skin surface SS, which is opposite to the concave portion 41*c*, to be likely mobile, so that the movement of the measurement portion MP of the human body is emphasized.

Therefore, the data processing unit 3 (see FIG. 1) can easily detect the movement component of the human body on the basis of the infrared light irradiated from the infrared LED 33 to the part of the skin surface SS through the concave portion 41*c*.

As a result, even if at least one of the intensity and the amount of the infrared light from the infrared LED 33 is lower as compared with the infrared LED 17 according to the first embodiment, it is possible to keep high the measuring sensitivity of the movement component of the human body, allowing the power consumption of the pulse wave sensor 31 to be saved.

In a modification of this fourth embodiment, the outer end surface 51 of a transparent window wall 50 of a pulse wave sensor 31*a*, which corresponds to the transparent window wall 38*c*, is composed of a first surface 51*a* opposite to at least the green LED 35, and a second surface 51*b* opposite to at least the infrared LED 33.

The second surface 51*b* is formed with concave and convex portions 53*a* and 53*b*, so that, when the first surface 41*a* contacts to the skin surface SS of the measurement portion MP of the human body, the concave portions 53*b* provide a plurality of gaps G1 with respect to the skin surface SS.

That is, when the pulse wave sensor 31*a* is fitted to the measurement portion MP so that the first surface 51*a* of the transparent window wall 50 contacts to the skin surface SS of the measurement portion MP, the gaps G1 allows the concave portions 51*b* of the transparent window wall 51 not to directly contact to the human body.

This structure enables parts of the skin surface SS, which are opposite to the gaps G1, to be likely mobile, so that the movement of the measurement portion MP of the human body is emphasized.

Therefore, as well as the fourth embodiment, the data processing unit 3 (see FIG. 1) can easily detect the movement component of the human body, and it is possible to save the power consumption of the pulse wave sensor 31*a*.

Fifth Embodiment

A fifth embodiment of the present invention will be described hereinafter.

In the fifth embodiment, elements of a pulse wave sensor according to the fifth embodiment that are the same as those of the pulse wave sensor 31 according to the fourth embodiment are omitted or simplified.

Figure 14:
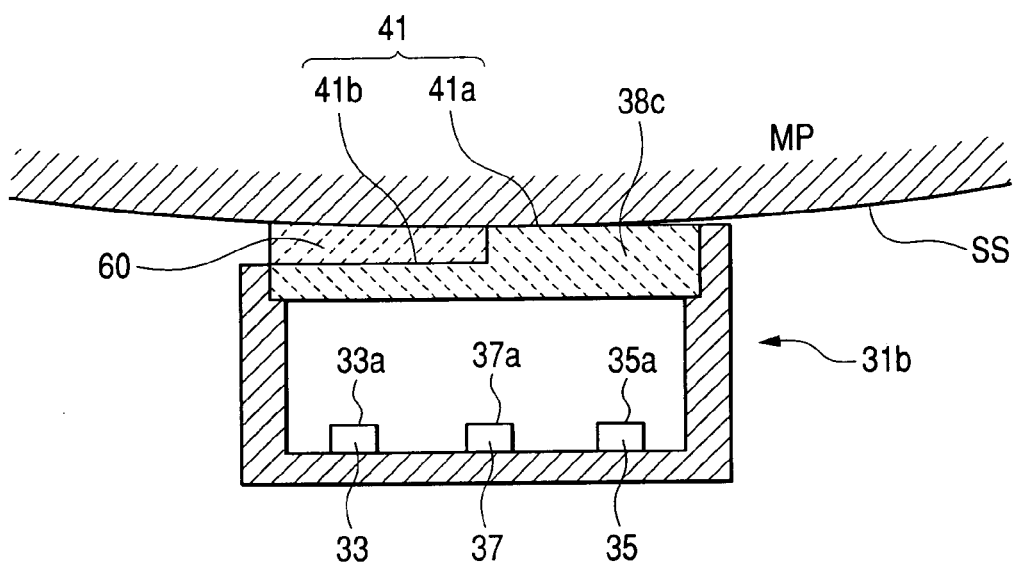
FIG. 14 is an enlarged view illustrating a pulse wave sensor according to a fifth embodiment of the present invention.

As shown in FIG. 14, the pulse wave sensor 31*b* according to the fifth embodiment is provided with a surface layer 60 made of, for example, transparent, translucent, and flexible material, such as gel silicon. The surface layer 60 is fittedly disposed in the concave portion 41*c* so that an outer end surface of the surface layer 60 is continuous with the first surface 41*a*.

In this fifth embodiment, when the pulse wave sensor 31*b* is fitted to the measurement portion MP so that the first surface 41*a* of the transparent window wall 38*c* with translucency contacts to the skin surface SS of the measurement portion MP, the surface layer 60 directly contacts to the human body.

Because the surface layer 60 is made of transparent flexible material, the surface layer 60 enables a part of the skin surface SS, which contacts to the surface layer 60, to be easily mobile, so that the movement of the measurement portion MP of the human body is emphasized.

Therefore, as well as the fourth embodiment, the data processing unit 3 (see FIG. 1) can easily detect the movement component of the human body, and it is possible to save the power consumption of the pulse wave sensor 31*b*.

Incidentally, surface layers each made of transparent flexible material may be fittedly disposed in the concave portions (gaps) 53*a* of the pulse wave sensor 31*a*, which obtains identical effects of the fifth embodiment.

Sixth Embodiment

A sixth embodiment of the present invention will be described hereinafter.

In the sixth embodiment, elements of a pulse wave sensor according to the sixth embodiment that are the same as those of the pulse wave sensor 5 according to the first embodiment are omitted or simplified.

Figure 15:
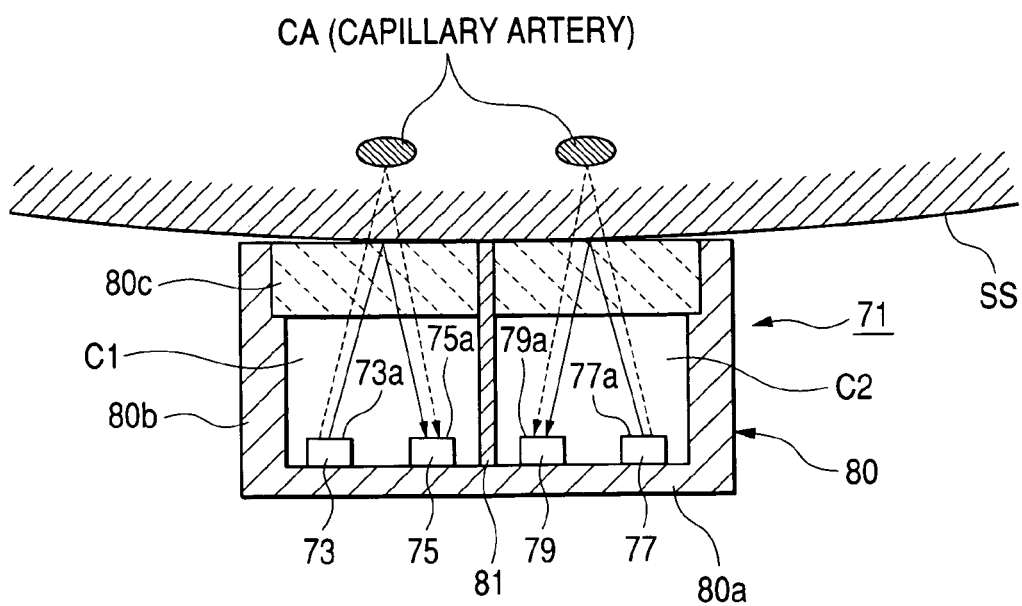
FIG. 15 is an enlarged view illustrating a pulse wave sensor according to a sixth embodiment of the present invention.

As shown in FIG. 15, the pulse wave sensor 71 according to the sixth embodiment is composed of two pair of LED and PD.

That is, the pulse wave sensor 71 is composed of, as a first pair of LED and PD, an infrared LED 73 with its emitting portion 73*a* corresponding to the infrared LED 17, and a first PD 75 with its light sensitive portion 75*a* corresponding to the PD 21. The first PD 75 is configured to only detect the reflected light based on the infrared light.

In addition, the pulse wave sensor 71 is also composed of as a second pair of LED and PD, a green LED 77 with its emitting portion 77*a* corresponding to the green LED 19, and a second PD 79 with its light sensitive portion 79*a* corresponding to the PD 21. The second PD 79 is configured to only detect the reflected light based on the green light.

Similarly, the pulse wave sensor 71 is provided with a housing 80 corresponding to the housing 23. The housing 80 is composed of a bottom wall 80*a* corresponding to the bottom wall 23*a*, a side wall portion 80*b* corresponding to the side wall portion 23*b*, and a transparent window wall 80*c* corresponding to the transparent window wall 23*c*.

In this sixth embodiment, the infrared LED 73, the first PD 75, the green LED 77, and the second PD 79, as shown in FIG. 15, are mounted on the inner surface of the bottom wall 80*a* of the housing 80. The infrared LED 73, the first PD 75, the second PD 79, and the green LED 77 are arranged in a row in this order so that the first PD 75 is interposed between the infrared LED 17 and the green LED 19, and the second PD 79 is interposed between the first PD 75 and the green LED 77.

In addition, the housing 80 is also provided with a partition wall 81 made of lightproof material. The partition wall 81 is mounted at its one end portion on the inner surface of the bottom wall 80*a* to be located between the first PD 75 and the second PD 79.

The partition wall 81 extends toward the transparent window wall 80*c* so that its other end portion is penetrated through the transparent window wall 80*c* to be fixed thereto.

That is, the partition wall 81 is configured to partition the inner chamber of the housing 80 into a first chamber C1 containing the first pair of infrared LED 73 and first PD 75, and a second chamber C2 containing the second pair of green LED 77 and second PD 79.

In this sixth embodiment, the housing 80 is partitioned by the partition wall 81 into the first and second chambers C1 and C2 so that the first pair of infrared LED 73 and first PD 75 contained in the first chamber C1 are optically isolated from the second pair of green LED 77 and second PD 79 contained in the second chamber C2.

As a result, even when the infrared LED 73 and the green LED 77 simultaneously emit the infrared light and the green light, the reflected light based on the infrared light and the reflected light based on the green light are individually detected by the first PD 75 and the second PD 79.

Consequently, in the sixth embodiment, the infrared LED 73 and the green LED 79 can simultaneously emit the infrared light and the green light, respectively, making it possible to save the pulse wave measuring time.

Incidentally, the present invention is not limited to the above embodiments and their modifications, and may be applied in various modifications within the scope of the present invention.

For example, in the above embodiments and their modifications, the biological condition measuring apparatuses are explained. The pulse wave measuring program itself, however, including the pulsebeat component procedure and/or movement component extracting procedure shown in Step S100-S160 may be applied to a program product or a storage medium on which the pulse wave measuring program is installed.

As the storage medium, an electric control unit (ECU) designed to a microcomputer, a microchip, a flexible disk, a hard disk, a DVD (Digital Versatile Disk), or an optical disk may be available. That is, various kinds of storage mediums each on which the wave measuring program are installed may be used as modifications of the present invention.

The pulse wave measuring program may be applied to a program communicated through a communication line, such as internet.

Moreover, in the embodiments and their modifications, the detection signals based on the infrared light and the green light and detected by the pulse wave sensor are directly inputted to the data processing unit.

However, the detection signals may be inputted through a terminal, such as personal computer, and a network such as the internet to which the terminal linked, to the data processing unit far from the pulse wave sensor and linked to the internet. That is, based on the detection signals transmitted through the internet to the data processing unit, the data processing unit may execute the pulse wave measuring processes to measure the pulsebeat component (pulse rate) and/or the movement component.

Moreover, in the embodiments and their modifications, the infrared LED and the green LED are used for emitting the lights having the different wavelengths, respectively. However, other light emitting devices capable of emitting lights having different wavelengths, respectively, may be used in place of the infrared LED and the green LED.

In addition, in the embodiments and their modifications, the wavelength of the infrared light is set to approximately 940 nm, and that of the green light is set to approximately 520 nm. In the present invention, however, the wavelength of the infrared light may be set within approximately the range from 780 nm to 1000 nm, and the wavelength of the green light may be set within approximately the range from 460 nm to 570 nm.

These ranges of the wavelengths of the infrared light and the green light can clearly represent the characteristics illustrated in FIGS. 5A and 5B, thereby easily extracting the pulsebeat component and/or the movement component, and therefore, accurately obtaining the pulse rate and the interval of the adjacent pulsebeats.

Moreover, in the first embodiment, the intensity of the infrared light is set to be one-fifth (20%) of that of the green light. In the present invention, however, the intensity of the infrared light may be set to not more than 70% of that of the green light.

The range of the intensity of the infrared light can clearly represent the characteristics illustrated in FIGS. 5A and 5B, thereby easily extracting the pulsebeat component and/or the movement component, and therefore, accurately obtaining the pulse rate and the interval of the adjacent pulsebeats.

In addition, in the modification of the first embodiment, the amount of the infrared light is set to be one-fifth (20%) of that of the green light. In the present invention, however, the amount of the infrared light may be set to not more than 70% of that of the green light.

The range of the amount of the infrared light can clearly represent the characteristics illustrated in FIGS. 5A and 5B, thereby easily extracting the pulsebeat component and/or the movement component, and therefore, accurately obtaining the pulse rate and the interval of the adjacent pulsebeats.

Furthermore, in the second embodiment, the second gain corresponding to the infrared light is set to be one-fifth (20%) of the first gain corresponding to the green light. In the present invention, however, the second gain corresponding to the infrared light may be set to not more than 70% of the first gain corresponding to the green light.

These range of the second gain corresponding to the infrared light can clearly represent the characteristics illustrated in FIGS. 5A and 5B, thereby easily extracting the pulsebeat component and/or the movement component, and therefore, accurately obtaining the pulse rate and the interval of the adjacent pulsebeats.

While there has been described what is at present considered to be the embodiments and modifications of the invention, it will be understood that various modifications which are not described yet may be made therein, and it is intended to cover in the appended claims all such modifications as fall within the true spirit and scope of the invention.

This application is based upon and claims the benefit of priority of the prior Japanese Patent Application 2003-54581 filed on Feb. 28, 2003 so that the contents of which are incorporated herein by reference.

What is claimed is:

1. A biological condition measuring apparatus for measuring a biological condition of a living body, said apparatus comprising:

a light emitting unit configured to emit individually first and second lights to a measurement portion of the living body, said first and second lights having first and second wavelengths, respectively, said first and second wavelengths being different from each other;

a light receiving unit configured to receive first and second reflection lights to generate first and second detection signals based on the first and second reflection lights, respectively, said first reflection light being based on the first light reflected from the measurement portion, said second reflection light being based on the second light reflected from the measurement portion, said first and second detection signals having different characteristics from each other due to the difference between the first and second wavelengths; and a measuring unit configured to measure the biological condition based on the different characteristics of the first and second detection signals, wherein said first wavelength is longer than the second wavelength, said light emitting unit is configured to control that at least one of an intensity and an amount of the first light is lower than at least one of an intensity and an amount of the second light, and said different characteristics of the first and second detection signals are based on the difference of the first and second wavelengths, and the difference between the at least one of the intensity and the amount of the first light and the at least one of the intensity and the amount of the second light.

2. A biological condition measuring apparatus according to claim 1, wherein said measuring unit is configured to compare the characteristic of the first detection signal with that of the second detection signal, and to extract a signal from the first and second detection signals according to a result of the comparing, said extracted signal representing the biological condition.

3. A biological condition measuring apparatus according to claim 1, wherein said biological condition includes a pulsebeat component and a component of a movement of the living body, said pulsebeat component being synchronized with a heartbeat of the living body, said light emitting unit is configured to sequentially emit the first and the second lights, said light receiving unit is configured to receive the first and second reflection lights sequentially reflected from the measurement portion, and to sequentially transmit the first and second detection signals to the measuring unit, and said measuring unit comprises:

a convening circuit configured to convert the transmitted first and second detection signals into first and second digitized sequential data, said first digitized sequential data corresponding to the first light, said second digitized sequential data corresponding to the second light;

a frequency-analyzing unit configured to frequency-analyze the first and second digitized sequential data, respectively, to obtain first and second frequency components from the first digitized sequential data, and third and fourth frequency components from the second digitized sequential data, said first and third frequency components representing the pulsebeat component, said second and fourth frequency components representing the component of the living body's movement; and an obtaining unit configured to obtain a frequency of at least one of the pulsebeat component and the component of the living body's movement according to the obtained first, second, third, and fourth frequency components.

4. A biological condition measuring apparatus according to claim 1, wherein one of said first and second lights is an infrared light, and other thereof is green light.

5. A biological condition measuring apparatus according to claim 1, wherein said light emitting unit includes at least two light emitting devices configured to emit the first and second lights, respectively, and said light receiving unit includes at least one receiving element configured to receive the first and second reflection lights, respectively.

6. A biological condition measuring apparatus according to claim 5, wherein said at least two light emitting devices are configured to emit the first and second lights at different timings, respectively.

7. A biological condition measuring apparatus according to claim 5, further comprising a driving unit configured to drive the at least two light emitting devices while changing the intensity of the first light with respect to that of the second light.

8. A biological condition measuring apparatus according to claim 1, further comprising a housing having a first wall, a second opened wall opposite to the first wall, and a window wall fitted to the second opened wall, wherein said light emitting unit is contained in the housing and configured to emit individually the first light and the second light trough the window wall to the measurement portion of the living body, said light receiving unit is contained in the housing, and said first reflection light being based on the first light reflected through the window wall from the measurement portion, said second reflection light being based on the second light reflected through the window wall from the measurement portion.

9. A biological condition apparatus according to claim 8, wherein said window wall is provided at its an outer end surface with a stepped portion, said stepped portion includes a first surface, and a second surface through which the first light and the first reflection light are transmitted, said stepped surface being stepped inwardly with respect to the first surface.

10. A biological condition apparatus according to claim 8, wherein said window wall has an outer end surface, said outer end surface includes a first surface and a second surface through which the first light and the first reflection light are transmitted, and said second surface is formed with concave and convex portions.

11. A biological condition apparatus according to claim 8, wherein said light emitting unit includes first and second light emitting devices configured to emit the infrared and green lights, respectively, said light receiving unit includes first and second receiving elements configured to receive the first and second reflection lights, respectively, and said housing is provided with a partition wall mounted at its one end portion on the first wall and its other end portion is fixed to the temperate window wall, thereby partitioning an inner chamber of the housing into a first chamber and a second chamber, said partition wall being made of lightproof material, said first chamber containing the first light emitting device and the first receiving element, said second chamber containing the second emitting device and the second receiving unit.

12. A biological condition measuring apparatus according to claim 1, wherein said light receiving unit includes a sensitivity changing unit configured to change a sensitivity of the first detection signal with respect to that of the second detection signal, thereby extracting a signal representing the biological condition from the first and second detection signals according to the different characteristics of the first and second detection signals, said different characteristics of the first and second detection signals being based on the difference between the first and second wavelengths and the difference between the sensitivities of the first and second detection signals.

13. A biological condition measuring apparatus according to claim 12, wherein said sensitivity changing unit is configured to amplify the first detection signal by a first gain, and the second detection signal by a second gain, said first and second gains being different from each after and corresponding to the sensitivities of the first and second detection signals, and to extract the signal representing the biological condition from the amplified first and second detection signals.

14. A biological condition measuring apparatus according to claim 13, wherein said first wavelength is longer than the second wavelength, and said first gain is lower than the second gain.

15. A biological condition measuring apparatus according to claim 14, wherein said measuring unit is configured to compare the amplified first detection signal with the amplified second detection signal, and to extract a signal from the first and second detection signals according to a result of the comparing, said extracted signal representing the biological condition.

16. A sensor for sensing a biological condition of a living body, said sensor comprising:

a housing having a first wall, a second opened wall opposite to the first wall, and a window wall fitted to the second opened wall; and the biological condition measuring apparatus according to claim 2, the biological condition measuring apparatus being contained in the housing, wherein said window wall is provided at its an outer end surface with a stepped portion, said stepped portion includes a first surface, and a second surface through which the first light and the first reflection light are transmitted, said stepped surface being stepped inwardly with respect to the first surface.

17. A sensor according to claim 16, further comprising a flexible member having translucency and arranged on the stepped surface of the window wall.

18. A sensor for sensing a biological condition of a living body, said sensor comprising:

a housing having a first wall, a second opened wall opposite to the first wall, and a window wall fitted to the second opened wall; and the biological condition measuring apparatus according to claim 2, the biological condition measuring apparatus being contained in the housing, wherein said window wall has an outer end surface, said outer end surface includes a first surface and a second surface through which the first light and the first reflection light are transmitted, and said second surface is formed with concave and convex portions.

19. A biological condition measuring apparatus for measuring a biological condition of a living body, said apparatus comprising:
- a light emitting unit configured to emit individually an infrared light and a green right to a measurement portion of the living body;
- a light receiving unit configured to receive first and second reflection lights to generate first and second detection signals based on the first and second reflection lights, respectively, said first reflection light being based on the infrared light reflected from the measurement portion, said second reflection light being based on the green light reflected from the measurement portion, said first and second detection signals having different characteristics from each other due to the difference between wavelengths of the infrared light and the green light; and
- a measuring unit configured to measure the biological condition based on the different characteristics of the first and second detection signals,
- wherein said light emitting unit is configured to control tat at least one of an intensity and an amount of the infrared light is lower than at least one of an intensity and an amount of the green light, and said different characteristics of the first and second detection signals are based on the difference of the wavelengths of the infrared light and the green light, and the difference between the at least one of the intensity and the amount of the infrared light and the at least one of the intensity and the amount of the green light.

20. A biological condition measuring apparatus according to claim 19, wherein said wavelength of the green light is set within a range from approximately 460 nm to approximately 570 nm, and said wavelength of the infrared light is set within a range from approximately 780 nm to approximately 1000 nm.

21. A biological condition measuring apparatus according to claim 19, wherein said intensity of the infrared light is not mote than 70 percent of the intensity of the green light.

22. A biological condition measuring apparatus according to claim 19, wherein said biological condition includes a pulsebeat component and a component of a movement of the living body, said pulsebeat component being synchronized with a heartbeat of the living body, said light emitting unit is configured to sequentially emit the infrared and green lights, said light receiving unit is configured to receive the first and second reflection lights sequentially reflected from the measurement portion, and to sequentially obtain the first and second detection signals to the measuring unit, and said measuring unit comprises:
- a converting circuit configured to convert the transmitted first and second detection signals into first and second digitized sequential data, said first digitized sequential data corresponding to the infrared light, said second digitized sequential data corresponding to the green light;
- a frequency-analyzing unit configured to frequency-analyze the first and second digitized sequential data, respectively, to obtain first and second frequency components from the first digitized sequential data, and third and fourth frequency components from the second digitized sequential data, said first and third frequency component representing the pulsebeat component, said second and fourth frequency components representing the component of the living body's movement; and
- an obtaining unit configured to obtain a frequency of at least one of the pulsebeat component and the component of the living body's movement according to the obtained first, second, third, and fourth frequency components.

23. A biological condition measuring apparatus according to claim 22, wherein said obtaining unit is configured to obtain the frequency of the pulsebeat component and to obtain at least one of a pulse rate and an interval between adjacent pulsebeats based on the frequency of the pulsebeat component.

24. A biological condition measuring apparatus according to claim 19, wherein said light emitting unit includes at least two light emitting devices configured to emit the infrared and green lights, respectively, and said light receiving unit includes at least one receiving element configured to receive the first and second reflection lights, respectively.

25. A biological condition measuring apparatus according to claim 24, wherein said at least two light emitting devices are configured to emit the infrared and green lights at different timings, respectively, and said at least one receiving element is configured to receive the first and second reflection lights, respectively.

26. A biological condition measuring apparatus according to claim 19, further comprising a driving unit configured to drive the at least two light emitting devices while changing the intensity of the infrared light with respect to that of the green light.

27. A biological condition measuring apparatus according to claim 19, wherein said light receiving unit includes a sensitivity changing unit configured to change a sensitivity of the first detection signal with respect to that of the second detection signal, thereby extracting a signal representing the biological condition from the first and second detection signals based on the different characteristics of the first and second detection signals, said different characteristics of the first and second detection signals being based on the difference between the wavelengths of the infrared and green light, and the difference between the sensitivities of the first and second detection signals.

28. A method of measuring a biological condition of a living body, said method comprising:
- individually emitting first and second lights to a measurement portion of the living body, said first and second lights having first and second wavelengths, respectively, said first and second wavelengths being different from each other;
- receiving first and second reflection lights to generate first and second detection signals based on the first and second reflection lights, respectively, said first reflection light being based on the first light reflected from the measurement portion, said second reflection light being based on the second light reflected from the measurement portion, said first and second detection signals having different characteristics from each other due to the difference between the first and second wavelengths; and
- measuring the biological condition based on the different characteristics of the first and second detection signals,
- wherein said first wavelength is longer than the second wavelength, said emitting step includes controlling that at least one of an intensity and an amount of the first light is lower than at least one of an intensity and an amount of the second light, and said different characteristics of the first and second detection signals are based on the difference of the first and second wavelengths, and the difference between the at least one of the intensity and the amount of the first light and the at least one of the intensity and the amount of the second light.

29. A method according to claim 28, wherein said receiving step includes changing a sensitivity of the first detection signal with respect to that of the second detection signal, thereby extracting a signal representing the biological condition from the first and second detection signals according to the different characteristics of the first and second detection signals, said different characteristics of the first and second detection signals being based on the difference of the first and second wavelengths and the difference between the sensitivities of the first and second detection signals.

30. A method according to claim 28, wherein said biological condition includes a pulsebeat component and a component of a movement of the living body, said pulsebeat component being synchronized with a heartbeat of the living body, said light emitting unit is configured to sequentially emit the first and the second lights, said receiving step includes receiving the first and second reflection lights sequentially reflected from the measurement portion, and sequentially generating the first and second detection signals, and said measuring step includes:

converting the generated first and second detection signals into first and second digitized sequential data, said first digitized sequential data corresponding to the first light, said second digitized sequential data corresponding to the second light;

frequency-analyzing the first and second digitized sequential data, respectively, to obtain first and second frequency components from the first digitized sequential data, and third and fourth frequency components from the second digitized sequential data, said first and third frequency component representing the pulsebeat component, said second and fourth frequency components representing the component of the living body's movement; and obtaining a frequency of at least one of the pulsebeat component and the component of the living body's movement according to the obtained first, second, third, and fourth frequency components.

31. A method according to claim 28, wherein said receiving step includes changing a sensitivity of the first detection signal with respect to that of the second detection signal, thereby extracting a signal representing the biological condition front the first and second detection signals according to the different characteristics of the first and second detection signals, said different characteristics of the first and second detection signals being based on the difference of the first and second wavelengths and the difference between the sensitivities of the first and second detection signals.

32. A program product readable by a computer communicable with a light emitting unit and a light receiving unit, said light emitting unit being configured to emit individually first and second lights to a measurement portion of the living body, said first and second lights having first and second wavelengths, respectively, said first and second wavelengths being different from each other, said light receiving unit being configured to receive first and second reflection lights to generate first and second detection signals based on the first and second reflection lights, respectively, said first reflection light being based on the first light reflected from the measurement portion, said second reflection light being based on the second light reflected from the measurement portion, said first and second detection signals having different characteristics from each other due to the difference between the first and second wavelengths, said program product configured to cause the computer to:

control the light emitting unit so that the light emitting unit controls that at least one of an intensity and an amount of the first light is lower than at least one of an intensity and an amount of the second light, said different characteristics of the first and second detection signals being based on the difference of the first and second wavelengths, and the difference between the at least one of the intensity and the amount of the first light and the at least one of the intensity and the amount of the second light;

compare the characteristic of the first detection signal with that of the second detection signal; and extract a signal from the first and second detection signals according to a result of the comparing, said extracted signal representing the biological condition.

* * * * *